US00PP12403P2

(12) United States Plant Patent
Small

(10) Patent No.: US PP12,403 P2
(45) Date of Patent: Feb. 12, 2002

(54) STRAWBERRY PLANT NAMED 'CAL GIANT 3'

(75) Inventor: David W. Small, Arroyo Grande, CA (US)

(73) Assignee: California Giant, Inc., Watsonville, CA (US)

( * ) Notice: Subject to any disclaimer, the term of this patent is extended or adjusted under 35 U.S.C. 154(b) by 0 days.

(21) Appl. No.: 09/379,680

(22) Filed: Aug. 24, 1999

(51) Int. Cl.[7] ..... A01H 5/00
(52) U.S. Cl. ..... Plt./209
(58) Field of Search ..... Plt./208, 209

(56) References Cited

U.S. PATENT DOCUMENTS

PP5,262 P 7/1984 Voth et al.
PP5,266 P 7/1984 Bringhurst et al.
PP7,614 P 8/1991 Bringhurst et al.
PP8,708 P 5/1994 Voth et al.
PP9,320 P 10/1995 Small et al.
PP10,451 P 6/1998 Shaw
PP10,461 P 6/1998 Shaw
PP10,960 P 6/1999 Lopez
PP10,982 P 6/1999 D'Ercole et al.

*Primary Examiner*—Bruce R. Campell
*Assistant Examiner*—Michelle Kizilkaya
(74) *Attorney, Agent, or Firm*—David A. Farah; Sheldon & Mak

(57) ABSTRACT

A new and distinct variety of strawberry plant named 'Cal Giant 3' that produces equivalent yields of equally high quality fruit in both fumigated and non-fumigated conditions, is resistant to many common foliar and soil borne diseases and pests, and has unusually execellent fruit flavor and aroma. Further, 'Cal Giant 3' has the potential to out-produce all currently grown varieties during the first half of the season, and to equal or exceed total season production of all currently grown varieties.

3 Drawing Sheets

BACKGROUND OF THE INVENTION

This new variety of stawberry, named 'Cal Giant 3', resulted from a cross performed in 1993 between proprietary plants designated 'C1' and 'NWFV'. Both the proprietary plants 'C1' and 'NWFV' were maintained exclusively for breeding purposes, were not released to growers and have not been the subject of an application for a plant patent in the United States.

'Cal Giant 3' was first selected as a seedling variety at the a breeding test plot in 1995 and has been propagated asexually by runners. It was originally designated '11D15' and later designated as advanced selection 'D3'. Asexual propagules from this original source have been tested at test plots throughout the various fruiting areas of Oxnard, Santa Maria and Watsonville, Calif., US. This propagation and testing has demonstrated that the combination of traits disclosed herein which characterize propagules of 'Cal Giant 3' are fixed and retained true to type through successive generations of asexual reproduction.

SUMMARY OF THE INVENTION

'Cal Giant 3' is a new and distinct strawberry variety characteristically different from any other strawberry variety. Among the characteristics that distinguish 'Cal Giant 3' are a combination of traits which include a strong everbearing tendency; natural resistance to many pests and foliar, fruit, and root diseases; and the production of a high number of exceptionally sweet fruit that are smoother than other commercial varieties. In addition, 'Cal Giant 2' produces equivalent yields of equally high quality fruit in both fumigated and non-fumigated conditions. Its fruit pollinates well in inclement weather conditions, allowing for continued production of well shaped, marketable fruit following cold and moist conditions. Further, 'Cal Giant 3' has the potential to out-produce all currently grown varieties during the first half of the season, and to equal or exceed total season production of all currently grown varieties.

BRIEF DESCRIPTION OF THE FIGURES

The accompanying color photographs show typical specimens of the new strawberry variety designated 'Cal Giant 3', including fruit, foliage and flower, as follows.

DETAILED BOTANICAL DESCRIPTION OF THE NEW VARIETY

Color terminology used herein is in accordance with the PANTONE® Color Formula Guide 1000 (Pantone Inc., 590 Commerce Boulevard, Carlstadt, N.J. US 07072-3098). The color descriptions and color illustrations are as nearly true as is reasonably possible. However, it is understood that both color and other phenotypic expressions described herein may vary from plant to plant with differences in growth, environmental and cultural conditions, without any change in the genotype of the variety 'Cal Giant 3'.

Unless specified otherwise, the 'Cal Giant 3' plants described below are for plants in mid-July, the ninth month of an annual planting scheme, and the fruit described are primary fruit.

Botanical Classification and Parentage

'Cal Giant 3' is a member of the genus Fragaria and species *ananassa*. It is a cross between proprietary plants designated 'C2', a female, and 'NWFV', a male.

Physical Description

Figure 1:
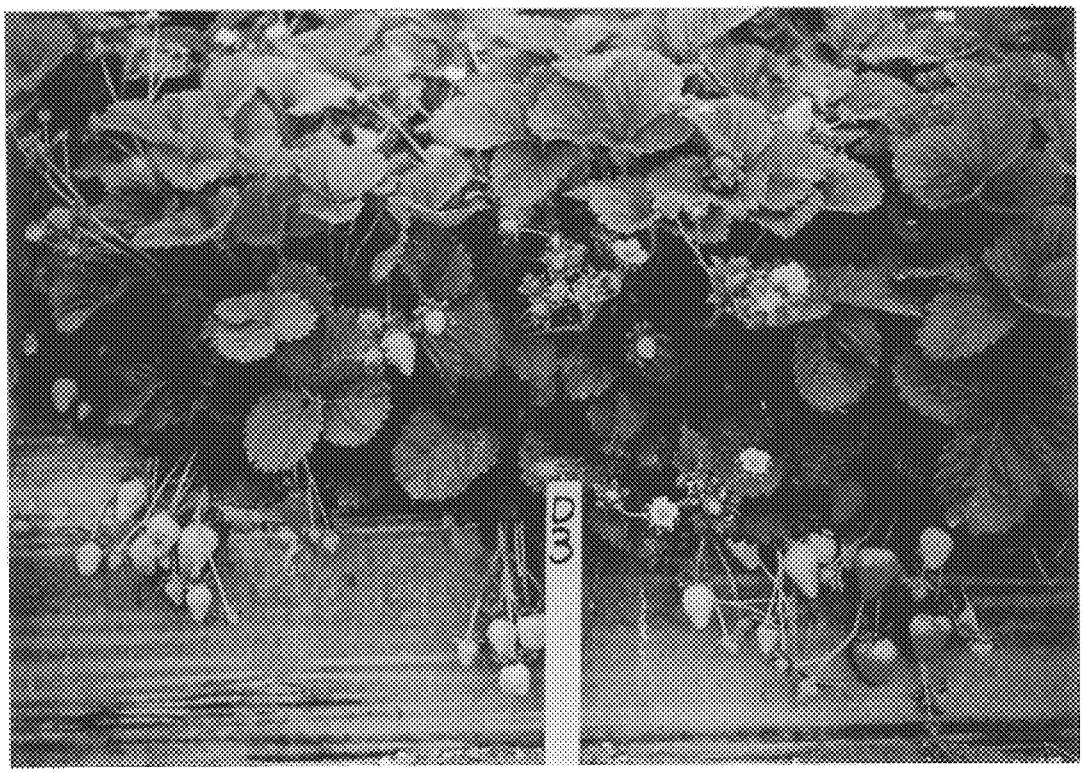
FIG. 1 is a color photograph taken in July 1998 showing general plant architecture, flowering, and fruiting characteristics.

Referring now to FIG. 1, there is shown a color photograph taken in July 1998 of 'Cal Giant 3' plants showing general plant architecture, flowering, and fruiting characteristics. As can be seen, fruiting plants of 'Cal Giant 3' grow in a semi-erect habit. 'Cal Giant 3' plants are as open but not as large as 'Catalina' U.S. Plant Pat. No. 9,320) and 'Seascape' (U.S. Plant Pat. No. 7,614) plants. Further, 'Cal Giant 3' plants are more erect than 'Cal Giant 2' (a proprietary plant which is the subject of a United States patent application filed Aug. 24, 1999), 'Camarosa' (U.S. Plant Pat. No. 8,708) and 'Selva' (U.S. Plant Pat. No. 5,266) plants.

As can be seen further in FIG. 1, the buds and fruit of 'Cal Giant 3' develop well away from the plant, advantageously easing harvest and allowing for good ventilation which reduces the incidence of fruit diseases. In general, 'Cal Giant 3' achieves a mid to late-season height of approximately 32 cm and a spread of approximately 64 cm. 'Cal Giant 3' has an upright fruiting habit with trusses drooping to the shoulder of the bed as fruit ripens. Average inflorescence length of 'Cal Giant 3' is 32.85 cm. Average peduncle length is 20.85 cm. Average pedicle length is 7.88 cm. Inflorescence length is longer than 'Cal Giant 2', 'Camarosa' and 'Selva', and shorter than 'Catalina', 'Chandler' (U.S. Plant Pat. No. 5,262) and 'Seascape'. The inflorescence tends to elongate as the plant grows larger throughout the season.

'Cal Giant 3' plants have mid-season leaf petioles averging 22.5 cm in length, making them less vigorous through mid-season than 'Catalina', 'Cal Giant 2' and 'Seascape' plants, and more vigorous than 'Selva'. Mid-season leaf petiole diameter averages 3.31 mm in width. Mid-season ternate (or trifoliate) leaves average 18.3 cm in width (measured across the widest area of the ternate leaf) and 10.3 cm in length (measured from the basal ternate connection to the primary leaf tip).

Leaf stipules are winged and average 3.38 cm in length from the base of the petiole to the tip of the stipule. Mature stipules are generally green to the tip, with some reddish to brown at the tip.

The leaves of 'Cal Giant 3' appear strong and healthy, with new leaves appearing above the existing canopy throughout the growing season. 'Cal Giant 3' canopy density is open. The leaves of 'Cal Giant 3' have a waxy cuticle, and about 15 to 25 serrations per leaflet, averaging 18.2 serrations per leaflet.

While stolons are not present during the fruiting season 'Cal Giant 3' runners profusely at plant nurseries in Northern California and Southern Oregon, producing 25 to 30 stolon per mother plant. Stolon produced by 'Cal Giant 3' lack pubescence and any appearance of anthocyanin. Crown size of plants produced along the stolon vary dependent upon stage of development. Average crown diameter of daughter plants produced along the stonon are less than or equal to 1 cm.

'Cal Giant 3' leaves tend to be lighter than 'Cal Giant 2', 'Camarosa', 'Catalina' or 'Selva', and darker than 'Chandler'. Visual comparisons of 'Cal Giant 3' leaf color to 'Cal Giant 2', 'Camarosa', 'Catalina' and 'Chandler' leaf color were made using the PANTONE® Color Formula Guide 1000 (Pantone Inc., 590 Commerce Boulevard, Carlstadt, N.J. US 07072-3098) and the results are given in Table I, below.

'Cal Giant 3' leaflets tend to be flat, orbicular in shape and to have dentate leaf margins. The leaflet base is cuneate. The leaflet apice are rounded. Leaflets of 'Cal Giant 3' are more orbicular than leaflets of 'Cal Giant 2', 'Catalina' and 'Seascape'.

'Cal Giant 3' plants display bract leaves on less than 5% of petioles. The bract leaves occur individually. The presence or absence of bract leaves and their size do not appear to be related to the stage of development of the primary leaves or to the size of the plant.

Tomentum is extremely sparse on 'Cal Giant 3' leaf petioles. When present, the hairs are less than 1 mm in length, curled and irregular in shape, and not firm. The tomentum lay at a 45° angle to the leaf petiole.

The buds, blooms, and fruit are borne on a dichasium cyme whose mid-season length averages 32.85 cm from the crown to the apice of the primary fruit. The five petals borne on each flower of 'Cal Giant 3' are completely white with no red pigmentation. The petals overlap and average 1.25 cm in length and 1.4 cm in width. The filament length ranges from 0.9 to 1.7 mm. The calyx of 'Cal Giant 3' is nonclasping, moderately to completely reflexed, and small to medium in size, averaging 3.83 cm in diameter. The sepals do not overlap, do not adhere to the berry and average 1.5 cm in length and 0.75 cm in width, and average 12 per calyx. Achene are present. Each receptacle bears hundreds of pistils.

There are 24 stamens per bloom, each bearing an anther measuring 1 mm in diameter. The stamens circle the receptacle in multiple tiers at random heights. The random dispersal of stamens distinguishes 'Cal Giant 3' from the 'Cal Giant 2', which has a single tier of stamens of the same height, and form 'Catalina', which has stamens in two distinct tiers of height.

Figure 2:
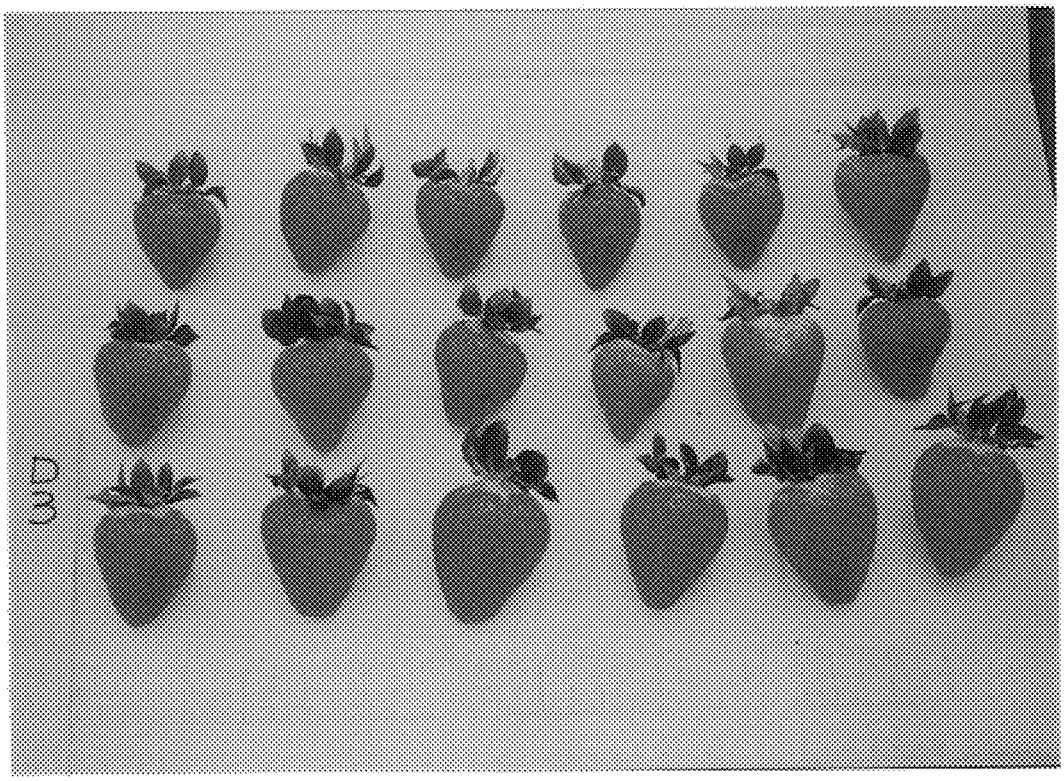
FIG. 2 is a color photograph showing a close-up view of the range of mature whole fruit.

The fruit of 'Cal Giant 3' are initially borne on single stems, branching to dichasium cymes in mid-season. The fruit is short conic and significantly smoother than both Cal Giant 2 and commercially grown varieties. The ratio of the width of the fruit to the length is 4.4:5. Referring now to FIG. 2, there is shown a color photograph showing a close-up view of the range of mature whole fruit.

'Cal Giant 3' produces a much higher number of well shaped, unblemished fruit than 'Camarosa', 'Catalina', 'Chandler' or 'Selva', averaging 45 berries per plant. 'Cal Giant 3' fruit are very well sized, averaging 31 grams per berry during the season. Advantageously, the difference in the size between primary, secondary and tertiary berries is much less than the difference in many other varieties, including 'Cal Giant 2', 'Catalina', 'Chandler' and 'Selva'.

'Cal Giant 3' fruit average 4.12 cm in length and 3.94 cm in width. The shoulder of 'Cal Giant 3' fruit ranges from very smooth to slightly necked. The fruit has a very high gloss. Its seeds are even with the fruit skin, and range in color from yellow to red, depending on the direction of the fruit in relation to the sun.

The skin and flesh of 'Cal Giant 3' fruit are very firm. The exterior fruit color of 'Cal Giant 3' is similar to 'Cal Giant 2' and lighter than the exterior fruit color of either 'Camarosa' or 'Catalina'. 'Cal Giant 3' fruit flesh displays good color saturation and the interior color substantially matches the exterior color. Visual comparisons of 'Cal Giant 3' fruit color were made with the fruit color of 'Cal Giant 2', 'Camarosa', 'Catalina' and 'Chandler' using the PANTONE® Color Formula Guide 1000 and the results are given in Table I, below.

TABLE 1

Visual Comparisons of 'Cal Giant 2' Leaf and Fruit Color to 'Catalina', 'Camarosa', and 'Chandler' Leaf and Fruit Color

| | Adaxial Leaf | Abaxial Leaf | External Fruit | Internal Fruit |
|---|---|---|---|---|
| 'Cal Giant 3' | 364U | 371U | 1788 U2X | 1788 U2X |
| 'Cal Giant 2' | 363U | 370U | Warm Red U2X | Warm Red U2X |
| 'Camarosa' | 349C | 348U | 193C | 185C |
| 'Catalina' | 342C | 348U–356U | 193C | 185C |
| 'Chandler' | 343C | 339U | 186C | 179C |

Additionally, the petiole, peduncle, and pedicel color of 'Cal Giant 3' is 576C.

Protein Characteristics

The isoenzyme content of 'Cal Giant 3' was compared with the isoenzyme content of six other varieties by gel electrophoresis. The results are given in Table II, below.

TABLE II

Comparisons of 'Cal Giant 3' Enzyme Content with the Enzyme Content of 'Aromas', 'Cal Giant 2', 'Catalina', 'Diamonte', 'Gaviota' and 'Pacifica'

| | Phosphoglucoseisomerase | Leucineaminopeptidase | Phosphoglucomutase |
|---|---|---|---|
| 'Cal Giant 3' | A3 | B3 | C2 |
| 'Aromas' | A4 | B3 | C2 |
| 'Cal Giant 2' | A3 | B3 | C2 |
| 'Catalina' | A4 | B3 | C4 |
| 'Diamonte' | A4 | B3 | C2 |
| 'Gaviota' | A2 | B3 | C1 |
| 'Pacifica' | A4 | B3 | C1 |

Flavor and Aroma of the Fruit

The flavor of 'Cal Giant 3' is exceptional. 'Cal Giant 3' fruit flavor displays a balance of sugars and acids similar to 'Catalina' and 'Chandler'. The soluble solid content, a measure of sugar content, of 'Cal Giant 3' fruit was determined to be 10.11% using a TY' MUP® 11-520-0 ATC Refractometer (TY' MUP PRODUCTS, a Division of Adcock Manufacturing Corporation, Gardena, Calif. 90249), compared to 'Cal Giant 2' (9.1%), 'Catalina' (8.29%), 'Selva' (8.64%), and 'Chandler' (7.5%).

Resistance to Diseases and Pests

'Cal Giant 3' plants are very healthy, displaying good natural resistance to many foliar, fruit, and root diseases, including Powdery Mildew (*Sphaerotheca macularis* spp. *fragariae*), Angular Leaf Spot (*Xanthomonas fragariae*), Phomopsis (*Dendrophoma obscurans*), Ramularia (or Mycosphaerella) leaf spot (*Ramularia tulasnet* or *Mycosphaerella fragariae*), as well as some Phytophthora spp. Further, 'Cal Giant 3' plants are resistant to many fungal diseases of fruit, such as Anthracnose (Colletotrichum spp.) and leather rot (*Phytophthora cactorum*).

Figure 3:
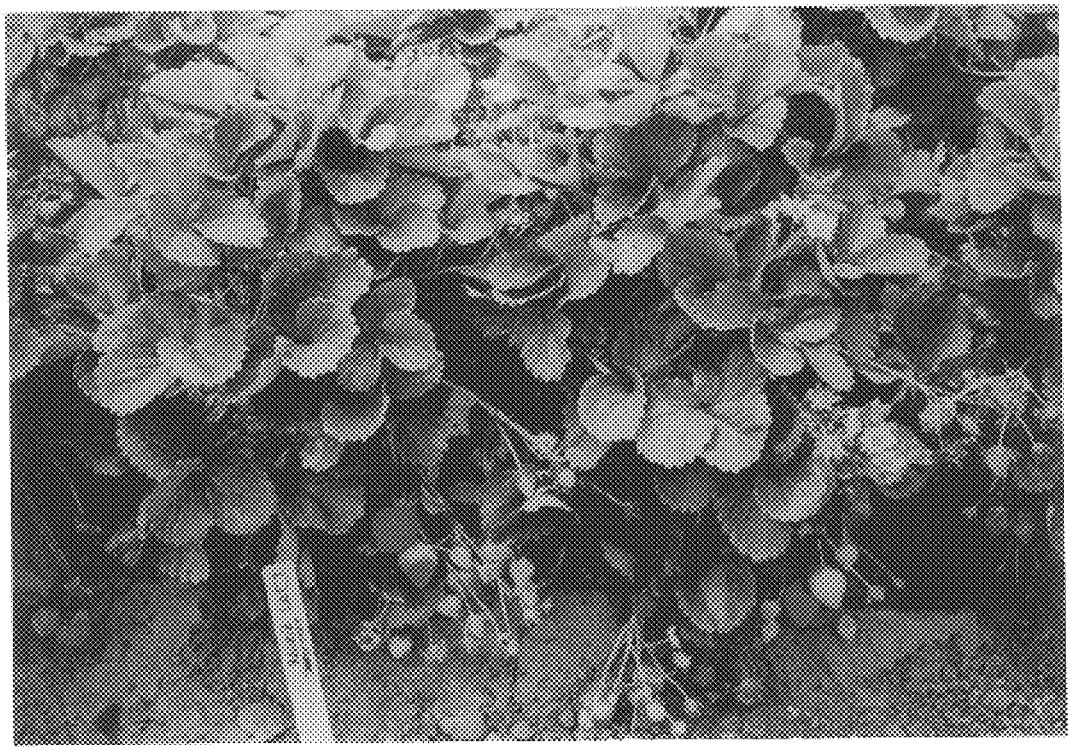
FIG. 3 is a color photograph taken in July 1998 showing the general plant architecture, flowering, and fruiting characteristics of plants grown in a non-fumigated, cultural system.

'Cal Giant 3' has been tested in non-fumigated conditions for several years and has also shown good natural resistance to soil borne diseases such as Verticillium wilt and Phytophthora spp. under these conditions. In non-fumigated conditions, 'Cal Giant 3' displays greater resistance than 'Aromas' (U.S. Plant Pat. No. 10,451), 'Cal Giant 2', 'Camarosa', 'Diamonte' (a University of California variety), 'Gaviota' (U.S. Plant Pat. No. 10,461), 'Pacifica' (a University of California variety), 'Seascape' and 'Selva' to soil borne diseases. Referring now to FIG. 3, there is shown a color photograph taken in July 1998 showing the general plant architecture, flowering, and fruiting characteristics of plants grown in a non-fumigated, cultural system.

Productivity Characteristics

'Cal Giant 3' is a strawberry cultivar with a strong everbearing tendency and advantageously produces equivalent yields of equally high quality fruit in both fumigated conditions and in non-fumigated conditions. Further advantageously, 'Cal Giant 3' has the potential to outproduce all currently grown varieties during the first half of the season, and to equal or exceed total season production of all currently grown varieties.

'Cal Giant 3' plants continue to produce high quality fruit well into the autumn months. They come into production similar to 'Catalina', and ahead of 'Cal Giant 2', 'Diamonte', 'Seascape' and 'Selva'.

'Cal Giant 3' initiates flowers in January in the Santa Maria and Watsonville, Calif. growing areas. Typically, harvest in both the these areas initiates in the second half of March. Production continues in Santa Maria, Calif. through July, and in Watsonville, Calif. through September. Typical production of 'Cal Giant 3' in Santa Maria, Calif. is 28.75 tons per acre. Typical production of 'Cal Giant 3' in Watsonville, Calif. is 34.5 tons per acre.

Advantageously, 'Cal Giant 3' is self-fertile, producing sufficient pollen throughout the season to insure very few malformed fruit. Further advantageously, 'Cal Giant 3' self pollinates well in inclement weather, thus facilitating significant early season production with few discarded fruit due to poor pollination.

What is claimed:

1. A new and distinct strawberry plant designated 'Cal Giant 3' as herein described and illustrated.

* * * * *